United States Patent [19]
Bandman et al.

[11] Patent Number: 5,922,318
[45] Date of Patent: Jul. 13, 1999

[54] UBIQUITIN CONJUGATION PROTEINS

[75] Inventors: Olga Bandman; Neil C. Corley, both of Mountain View; Preeti Lal; Purvi Shah, both of Sunnyvale, all of Calif.

[73] Assignee: Incyte Pharmaceuticals, Inc., Palo Alto, Calif.

[21] Appl. No.: 09/134,596

[22] Filed: Aug. 13, 1998

Related U.S. Application Data

[62] Division of application No. 08/861,269, May 21, 1997, Pat. No. 5,817,494.

[51] Int. Cl.$^6$ .............................. A61K 38/43; C12N 9/00
[52] U.S. Cl. ........................................... 424/94.1; 435/183
[58] Field of Search .............................. 435/183; 424/94.1

[56] References Cited

PUBLICATIONS

Hillier, L. et al., "Homo Sapiens cDNA Clone 754549 5' Similar to SW: UBC6_Yeast P33296 Ubiquitin–Conjugation Enzyme E2–28.4 KD", Emest Database Entry HS1206407, Accession No. AA411279, (May 4 1997), XP003078650.

Hiller, L. et al., "Homo Sapiens cDNA Clone 417998 5' Similar to SW: UBC6$_{13}$ Yeast P33296 Ubiquitin–Conjugation Enzyme E2–28.4 KD", EMEST Database Entry HSW6471, Accession No. W90647, (Jul. 9 1996), XP002078651.

Adams, M.D. et al., "Homo Sapiens cDNA Clone 5' Similar to Ubiquitin–Conjugating Enzyme" EMEST Database Entry HSZZ59197, Accession No. AA354073, (Apr. 18, 1997), XP002078652.

Hillier, L. et al., "Homo Sapiens cDNA Clone 728300", EMEST Database Entry HS1222367, Accession No. AA393664, (May 19, 1997), XP002078653.

Hillier, L. et al., "Homo Sapiens cDNA Clone 417998" EMEST Database Entry HSW6221, Accession No. W90622, (Jul. 9, 1996), XP002078654.

Wilson, R. et al., "2.2 MB of Contiguous Nucleotide Sequence from Chromosome III of C. Elegans", Nature, vol. 368, (1994), pp. 32–38, XP002050139.

Wilson, R. et al., "Caenorhabditis Elegans", SPTREMBL Database Entry Q19723, Accession No. Q19723, (Nov. 1, 1996).

Wilson, R. et al., "Caenorhabditis Elegans", EMINV Database Entry CED22D6, Accession No. Z71262, (Apr. 19, 1996).

Hillier, L. et al., "Homo Sapiens cDNA Clone 380898", EMEST Database Entry HSA56157, Accession No. AA056157, (Sep. 19, 1996), XP002078655.

Hillier, L. et al., "Homo Sapiens cDNA Clone 66240", EMEST Database Entry HS1151759, Accession No. AA233629, (Mar. 6, 1997), XP002078656.

Hillier, L. et al., Homo Sapiens cDNA Clone 321730 5'Similar to PIR:JN0673 Ubiquitin–Like Fusion Protein Anla–African Clawed Frog, EMEST Database Entry HS046352, Accession No. W33046, (May 16, 1996), XP002078657.

Ciechanover, A. et al., "The Ubiquitin–Proteasome Proteolytic Pathway", *Cell*, 79: 13–21 (1994).

Jentsch, S. "The Ubiquitin–Conjugation System", *Annu. Rev. Genet.*, 26: 179–207 (1992).

Monia, B.P. et al., "Gene Synthesis, Expression, and Processing of Human Ubiquitin Carboxyl Extension Proteins", *J. Biol. Chem.* 264: 4093–4099 (1989).

Sommer, T. et al., "A protein translocation defect linked to ubiquitin conjugation at the endoplasmic reticulum", *Nature*, 365: 176–179 (1993) (GI 397581).

Wilson, R. et al., (Direct Submission), GenBank Sequence Database (Accession Z71262), National Center for Biotechnology Information, National Library of Medicine, Bethesda, Maryland, 20894 (GI 1279275) (GI 1279278).

Shima, D.T. et al., "Alterations in gene expression associated with changes in the state of endothelial differentiation", *Differentiation*, 58: 217–226 (1995) (GI 998680).

Yoshioka, S., (Direct Submission), GenBank Sequence Database (Accession D89248), National Center for Biotechnology Information, National Library of Medicine, Bethesda, Maryland, 20894 (GI 1749703) (GI 1749704).

*Primary Examiner*—Robert A. Wax
*Assistant Examiner*—Elizabeth H. Slobodyansky
*Attorney, Agent, or Firm*—Sheela Mohan-Peterson; Lucy J. Billings; Incyte Pharmaceuticals, Inc.

[57] ABSTRACT

The present invention provides a human ubiquitin conjugation system protein (UCSP) and polynucleotides which encode UCSP. The invention also provides expression vectors, host cells, agonists, antisense molecules, antibodies, or antagonists. The invention also provides methods for treating disorders associated with expression of UCSP.

2 Claims, 16 Drawing Sheets

```
                       9            18            27            36            45            54
5' NNG  ATG  AGC  AGC  ACC  AGC  AGT  AAG  AGG  GCT  CCG  ACC  ACG  GCA  ACC  CAG  AGG  CTG
        M    S    S    T    S    S    K    R    A    P    T    T    A    T    Q    R    L 63            72            81            90            99           108
   AAG  CAG  GAC  TAC  CTT  CGC  ATT  AAG  GAC  CCG  GTG  CCT  TAC  ATC  TGT  GCC  GAG
    K    Q    D    Y    L    R    I    K    D    P    V    P    Y    I    C    A    E 117           126           135           144           153           162
   CCC  CTC  CCT  TCG  AAT  ATT  CTC  GAG  TGG  CAC  TAT  GTC  GTC  CGA  GGC  CCA  GAG  ATG
    P    L    P    S    N    I    L    E    W    H    Y    V    V    R    G    P    E    M 171           180           189           198           207           216
   ACC  CCT  TAT  GAA  GGT  GGC  TAT  TAT  CAT  GGA  AAA  CTA  ATT  TTT  CCC  AGA  GAA  TTT
    T    P    Y    E    G    G    Y    Y    H    G    K    L    I    F    P    R    E    F 225           234           243           252           261           270
   CCT  TTC  AAA  CCT  CCC  AGT  ATC  TAT  ATG  ATC  ACT  AAC  GGG  AGG  TTT  AAG  TGC
    P    F    K    P    P    S    I    Y    M    I    T    N    G    R    F    K    C 279           288           297           306           315           324
   AAC  ACC  AGG  CTG  TGT  CTT  TCT  ATC  ACG  GAT  TTC  CAC  CCG  GAC  ACG  TGG  AAC  CCG
    N    T    R    L    C    L    S    I    T    D    F    H    P    D    T    W    N    P
```

FIGURE 1A

```
      333         342         351         360         369         378
GCC TGG TCT GTC TCC ACC ATC CTG ACT GGG CTC CTG AGC TTC ATG GTG GAG AAG
 A   W   S   V   S   T   I   L   T   G   L   L   S   F   M   V   E   K 387         396         405         414         423         432
GGC CCC ACC CTG GGC AGT ATA GAG ACG TCG GAC TTC ACG AAA AGA CAA CTG GCA
 G   P   T   L   G   S   I   E   T   S   D   F   T   K   R   Q   L   A 441         450         459         468         477         486
GTG CAG AGT TTA GCA TTT AAT TTG AAA GAT AAA GTC TTT TGT GAA TTA TTT CCT
 V   Q   S   L   A   F   N   L   K   D   K   V   F   C   E   L   F   P 495         504         513         522         531         540
GAA GTC GTG GAG GAG ATT AAA CAA CAG AAA GCA CAA GAC GAA CTC AGT AGC
 E   V   V   E   E   I   K   Q   Q   K   A   Q   D   E   L   S   S 549         558         567         576         585         594
AGA CCC CAG ACT CTC CCC TTG CCA GAC GTG GTT CCA GAC GGG GAG ACG CAC CTC
 R   P   Q   T   L   P   L   P   D   V   V   P   D   G   E   T   H   L 603         612         621         630         639         648
GTC CAG AAC GGG ATT CAG CTG CTC AAC GGG CAT GCG CCG GGG GCC GTC CCA AAC
 V   Q   N   G   I   Q   L   L   N   G   H   A   P   G   A   V   P   N
```

FIGURE 1B

```
      657        666        675        684        693        702
CTC GCA GGG CTC CAG GCC AAC CGG CAC CAC GGA CTC CTG GGT GGC GCC CTG
 L   A   G   L   Q   A   N   R   H   H   G   L   L   G   G   A   L 711        720        729        738        747        756
GCG AAC TTG TTT GTG ATA GTT GGG TTT GCA GCC TTT GCT TAC ACG GTC AAG TAC
 A   N   L   F   V   I   V   G   F   A   A   F   A   Y   T   V   K   Y 765        774        783        792        801        810
GTG CTG AGG AGC ATC GCG CAG GAG TGA GGC CCA GGC CCA GGC GAG ACC CAA GGC GCC
 V   L   R   S   I   A   Q   E   *

819        828        837        846        855        864
ACT GAG GGC ACC GCG CAC CAG AGC CAG AGC TCG ACC GTG ACC TCG GCA GGC TGG ACA CAC TGC CCA 873        882        891        900        909        918
GCA CAG GCA GAC CCA CCA GGC TCC TAG GTT TAG CTT TTA AAA ACC TGA AAG GGG 927        936        945        954        963        972
AAG CAA AAA CCA AAA TGT GTG ACT GGG CTT TGG AGG AGA CTG GAG CCT CAG CCC
```

FIGURE 1C

```
        981         990         999        1008        1017        1026
TGT CCT GGC CAC GGG CCG CTG GGG CTG GTG TGG GTG GGC CTT GTG TGC TGG ATT 1035        1044        1053        1062        1071        1080
TGT AGC TTA TCT TCC GTG TTG TCT TTG GAC CTG TTT TAG TAA ACC CGT TTT TCA

TTT T 3'
```

FIGURE 1D.

```
                    9          18          27          36          45          54
5' NNN TCG GCG GCA TTA CCT GTA CCC ATT CAC CGG CTA CCG GCG GCG GCG CGC 63          72          81          90          99         108
AGT GTT CAG GCG GAG AGA CCC GCC GCC AGG AAT TGA ATC TGA AGT CTG CTG CAG 117         126         135         144         153         162
TAA AAC ACA GAA GGC TTT AAA ATG TTT TCT TGC ATA AAA TTC AAA ACT TTT AAG 171         180         189         198         207         216
TAG CTG CTT ATG AGA ATA GGG AAG GCA GAA AGC TAA TGT CTG TCT CAA GAT ACA 225         234         243         252         261         270
GGA CAG CTG TTT GCT CAT CAA CCT CAA CTG TGT GTG CAA CTG AGG AAC ATG GCT
                                                                 M   A 279         288         297         306         315         324
CAA GAA ACT AAT CAC AGC CAA GTG CCT ATG CTT TGT TCC ACT GGC TGT GGA TTT
 Q   E   T   N   H   S   Q   V   P   M   L   C   S   T   G   C   G   F
```

FIGURE 2A

```
TAT GGA AAC CCT CGT ACA AAT GGC ATG TGT TCA GTA TGC TAT AAA GAA CAT CTT
 Y   G   N   P   R   T   N   G   M   C   S   V   C   Y   K   E   H   L
333         342         351         360         369         378

CAA AGA CAG AAT AGT AGT AAT GGT AGA ATA AGC CCA CCT GCA ACC TCT GTC AGT
 Q   R   Q   N   S   S   N   G   R   I   S   P   P   A   T   S   V   S
387         396         405         414         423         432

AGT CTG TCT GAA TCT TTA CCA GTT CAA TGC ACA GAT GGC AGT GTG CCA GAA GCC
 S   L   S   E   S   L   P   V   Q   C   T   D   G   S   V   P   E   A
441         450         459         468         477         486

CAG TCA GCA TTA GAC TCT ACA TCT TCA TCT ATG CAG CCC AGC CCT GTA TCA AAT
 Q   S   A   L   D   S   T   S   S   S   M   Q   P   S   P   V   S   N
495         504         513         522         531         540

CAG TCA CTT TTA TCA GAA TCT GTA GCA TCT TCT TCT CAA TTG GAC AGT ACA TCT GTG
 Q   S   L   L   S   E   S   V   A   S   S   S   Q   L   D   S   T   S   V
549         558         567         576         585         594

GAC AAA GCA GTA CCT GAA ACA GAA GAT GTG CAG GCT TCA GTA TCA GAC ACA GCA
 D   K   A   V   P   E   T   E   D   V   Q   A   S   V   S   D   T   A
603         612         621         630         639         648
```

FIGURE 2B

```
      657            666            675            684            693            702
CAG CAG CCA TCT GAA GAG CAA AGC AAG TCT CTT GAA AAA CCG AAA CAA AAA AAG
 Q   Q   P   S   E   E   Q   S   K   S   L   E   K   P   K   Q   K   K 711            720            729            738            747            756
AAT CGC TGT TTC ATG TGC AGG AAG AAA GTG GGA CTT ACT GGG TTT GAA TGC CGG
 N   R   C   F   M   C   R   K   K   V   G   L   T   G   F   E   C   R 765            774            783            792            801            810
TGT GGA AAT GTT TAC TGT GGT GTA CAC CGT TAC TCA GAT GTA CAC AAT TGC TCT
 C   G   N   V   Y   C   G   V   H   R   Y   S   D   V   H   N   C   S 819            828            837            846            855            864
TAC AAT TAC AAA GCC GAT GCT GCT GAG AAA ATC AGA AAA GAA AAT CCA GTA GTT
 Y   N   Y   K   A   D   A   A   E   K   I   R   K   E   N   P   V   V 873            882            891            900            909            918
GTT GGT GAA AAG ATC CAA AAG ATT TGA ACT CCT GCT GGA ATA CAA AAT TCT TGA
 V   G   E   K   I   Q   K   I   *   T   P   A   G   I   Q   N   S   *

927            936            945            954            963            972
GCA TCT GCA AAC TAA AAA TTG ACT TGA GGT TTT TTT TTT CCT AGT CAT TGG GAA
```

FIGURE 2C

```
     981         990         999        1008        1017        1026
TGT AGA GCA GTG TAT CTT GCA TGT CAT CGG AAG AAT AGA TTT TTG TTT TGG TTT 1035        1044        1053        1062        1071        1080
TGT TTT GAA AAT GAC TCT GAA CAT TTA TTT CCA TTG CAA TTT CTG TGG CTG AGG 1089        1098        1107        1116        1125        1134
AGA CTT AAA CTT TAC AAG TAT TAT CCT TTT AAG ATC ATT TTA ATT TTA GTT GAG 1143        1152        1161        1170        1179        1188
TGC AGA GGG CTT TTA TAA CAA ACC GTG CAG AAA TTT TGG AGG GCT GTG ATT TTT

1197
CCA GTA TTA AAC  3'
```

FIGURE 2D

```
  1  MSSTSSKRAPTTATQRLKQDYLRIKKDPVPYICAEPLPSN   UCSP-1
  1  MATKQAHK-------RLTKEYKLMVENPPYILARPNEDN    g397581
  1  -------YK------RLMKEYLALQKNPFELVDAKPATEN   g1749704

41  ILEWHYVVRGPEMTPYEGGYYHGKLIFPREFPFKPPSIYM   UCSP-1
 34  ILEWHYIITGPADTPYKGGQYHGTLTFPSDYPYKPPAIRM   g397581
 28  ILEWHYIITGPPDTPYEGGQYHGTLIFPPDYPFKPPAIRM   g1749704

81  ITPNGRFKCNTRLCLSITDFHPDTWNPAWSVSTILTGLLS   UCSP-1
 74  ITPNGRFKPNTRLCLSMSDYHPDTWNPGWSVSTILNGLLS   g397581
 68  ITPSGRFQTNTRLCLSFSDFHPKSWNPSWMVSTILVGLVS   g1749704

121  FMVEKGPTLGSIETSDFTKRQLAVQSLAFNLKDKV-FCEL   UCSP-1
114  FMTSDEATTGSITTSDHQKKTLARNISYNTFQNVRFKLI    g397581
108  FMTSDEITTGGIVTSESTRRTYAKDTKRFNIMDNPKFLIM   g1749704
```

FIGURE 3A

```
160 FPEVVEEIKQ---KQKAQDELSSRPQTLPLPDVVPDGETH  UCSP-1
154 FPEVVQENVETLEK---RKLDEGDAANTGDETEDPFTKAAKEK  g397581
148 FPELIDKNREDIAK------------------AAAEAA  g1749704

197 LVQNGIQLLNGHAPGAVPNLAGLQQANRHHGLLGGALA-N  UCSP-1
194 VISLE-EILDPEDRIRAEQALRQSENNSKKD-GKEPNDSS  g397581
168 LIEPQ-QI--HSTPVSSNECKKNEPFNSKQSWVKSRWSIA  g1749704

236 LFVIVGFAAFAYTVKYVLRSIAQE------  UCSP-1
232 SMVYIGIAIELF---LVGLFMK------  g397581
205 VLVFFALALARF------FGA--DS  g1749704
```

FIGURE 3B

```
  1  MAQETNHSQVPMLCSTGCGFYGNPRTNGMCSVCYKEHLQR  UCSP-2
  1  MENEQQAQTAPSCRAGCGFFGASATEGYCSQCFKNTLKR   g1279278
  1  ---------------------------------------   g998680

41  QNSSNGRISPPATSVSSLSESLPVQCTDGSVPEAQSALDS  UCSP-2
 41  QQDT-VRLTSPVVSPSSMAAT--------SSALKS       g1279278
  1  ---------------------------------------   g998680

81  TSSSMQPSPVSNQSLLSESVASSQLDSTSVDKAVPETEDV  UCSP-2
 67  EPSSVD---MCMKAAVSVSDETAKMDCEDIINVCDQINDD  g1279278
  1  ---------------------------------------   g998680

121  QASVSDTAQQPSEEQSKSLEKPKQKKNRCFMCRKKVGLTG  UCSP-2
104  SVTVAEST--APTTITVDVPVPVKKANRCHMCKKRVGLTG  g1279278
  1  ---------------------------------------   g998680

161  FECRCGNVYCGVHRYSDVHNCSYNYKADAAEKIRKENPVV  UCSP-2
142  FSCRCGGLYCGDHRYDQAHNCQFDYKTMERETIRKNNPVV  g1279278
  1  --CRCGNLFCGLHRYSDKHNCPYDYKAEAAAKIRKENPVV  g998680

201  VGEKIQKI      UCSP-2
182  VSDKVQRI      g1279278
 39  VAEKIQRI      g998680
```

FIGURE 4

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 259 amino acids
      (B) TYPE: amino acid
      (C) STRANDEDNESS: single
      (D) TOPOLOGY: linear (vii) IMMEDIATE SOURCE:
      (A) LIBRARY: KERANOT02
      (B) CLONE: 2029018

(xi) SEQUENCE DESCRIPTION: SEQ ID NO:1:

```
Met Ser Ser Thr Ser Ser Lys Arg Ala Pro Thr Thr Ala Thr Gln Arg
 1               5                  10                  15

Leu Lys Gln Asp Tyr Leu Arg Ile Lys Lys Asp Pro Val Pro Tyr Ile
                20                  25                  30

Cys Ala Glu Pro Leu Pro Ser Asn Ile Leu Glu Trp His Tyr Val Val
            35                  40                  45

Arg Gly Pro Glu Met Thr Pro Tyr Glu Gly Gly Tyr Tyr His Gly Lys
        50                  55                  60

Leu Ile Phe Pro Arg Glu Phe Pro Phe Lys Pro Pro Ser Ile Tyr Met
65                  70                  75                  80

Ile Thr Pro Asn Gly Arg Phe Lys Cys Asn Thr Arg Leu Cys Leu Ser
                85                  90                  95

Ile Thr Asp Phe His Pro Asp Thr Trp Asn Pro Ala Trp Ser Val Ser
            100                 105                 110

Thr Ile Leu Thr Gly Leu Leu Ser Phe Met Val Glu Lys Gly Pro Thr
        115                 120                 125

Leu Gly Ser Ile Glu Thr Ser Asp Phe Thr Lys Arg Gln Leu Ala Val
        130                 135                 140

Gln Ser Leu Ala Phe Asn Leu Lys Asp Lys Val Phe Cys Glu Leu Phe
145                 150                 155                 160

Pro Glu Val Val Glu Glu Ile Lys Gln Lys Gln Lys Ala Gln Asp Glu
                165                 170                 175

Leu Ser Ser Arg Pro Gln Thr Leu Pro Leu Pro Asp Val Val Pro Asp
                180                 185                 190

Gly Glu Thr His Leu Val Gln Asn Gly Ile Gln Leu Leu Asn Gly His
```

```
              195                200                 205
Ala Pro Gly Ala Val Pro Asn Leu Ala Gly Leu Gln Gln Ala Asn Arg
    210                 215                220

His His Gly Leu Leu Gly Gly Ala Leu Ala Asn Leu Phe Val Ile Val
225                 230                 235                240

Gly Phe Ala Ala Phe Ala Tyr Thr Val Lys Tyr Val Leu Arg Ser Ile
                245                 250                 255

Ala Gln Glu (2) INFORMATION FOR SEQ ID NO:2:

(i) SEQUENCE CHARACTERISTICS:
        (A) LENGTH: 1082 base pairs
        (B) TYPE: nucleic acid
        (C) STRANDEDNESS: single
        (D) TOPOLOGY: linear (vii) IMMEDIATE SOURCE:
        (A) LIBRARY: KERANOT02
        (B) CLONE: 2029018

(xi) SEQUENCE DESCRIPTION: SEQ ID NO:2:

GATGAGCAGC ACCAGCAGTA AGAGGGCTCC GACCACGGCA ACCCAGAGGC TGAAGCAGGA       60

CTACCTTCGC ATTAAGAAAG ACCCGGTGCC TTACATCTGT GCCGAGCCCC TCCCTTCGAA      120

TATTCTCGAG TGGCACTATG TCGTCCGAGG CCCAGAGATG ACCCCTTATG AAGGTGGCTA      180

TTATCATGGA AAACTAATTT TTCCCAGAGA ATTTCCTTTC AAACCTCCCA GTATCTATAT      240

GATCACTCCC AACGGGAGGT TTAAGTGCAA CACCAGGCTG TGTCTTTCTA TCACGGATTT      300

CCACCCGGAC ACGTGGAACC CGGCCTGGTC TGTCTCCACC ATCCTGACTG GCTCCTGAG       360

CTTCATGGTG GAGAAGGGCC CCACCCTGGG CAGTATAGAG ACGTCGGACT TCACGAAAAG      420

ACAACTGGCA GTGCAGAGTT TAGCATTTAA TTTGAAAGAT AAAGTCTTTT GTGAATTATT      480

TCCTGAAGTC GTGGAGGAGA TTAAACAAAA ACAGAAAGCA CAAGACGAAC TCAGTAGCAG      540

ACCCCAGACT CTCCCCTTGC AGACGTGGT TCCAGACGGG GAGACGCACC TCGTCCAGAA       600

CGGGATTCAG CTGCTCAACG GCATGCGCC GGGGGCCGTC CCAAACCTCG CAGGGCTCCA      660

GCAGGCCAAC CGGCACCACG GACTCCTGGG TGGCGCCCTG GCGAACTTGT TTGTGATAGT      720

TGGGTTTGCA GCCTTTGCTT ACACGGTCAA GTACGTGCTG AGGAGCATCG CGCAGGAGTG      780

AGGCCCAGGC GCCGAGACCC AAGGCGCCAC TGAGGGCACC GCGCACCAGA GCGTGACCTC      840

GGCAGGCTGG ACACACTGCC CAGCACAGGC AGACCCACCA GGCTCCTAGG TTTAGCTTTT      900

AAAAACCTGA AAGGGGAAGC AAAAACCAAA ATGTGTGACT GGGCTTTGGA GGAGACTGGA      960

GCCTCAGCCC TGTCCTGGCC ACGGGCCGCT GGGGCTGGTG TGGGTGGGCC TTGTGTGCTG     1020

GATTTGTAGC TTATCTTCCG TGTTGTCTTT GGACCTGTTT TAGTAAACCC GTTTTTCATT     1080

TT                                                                    1082

(2) INFORMATION FOR SEQ ID NO:3:

(i) SEQUENCE CHARACTERISTICS:
        (A) LENGTH: 208 amino acids
        (B) TYPE: amino acid
        (C) STRANDEDNESS: single
        (D) TOPOLOGY: linear (vii) IMMEDIATE SOURCE:
        (A) LIBRARY: BRAINOT09
        (B) CLONE: 2151473

(xi) SEQUENCE DESCRIPTION: SEQ ID NO:3:
```

```
Met Ala Gln Glu Thr Asn His Ser Gln Val Pro Met Leu Cys Ser Thr
 1               5                  10                  15

Gly Cys Gly Phe Tyr Gly Asn Pro Arg Thr Asn Gly Met Cys Ser Val
            20                  25                  30

Cys Tyr Lys Glu His Leu Gln Arg Gln Asn Ser Ser Asn Gly Arg Ile
            35                  40                  45

Ser Pro Pro Ala Thr Ser Val Ser Ser Leu Ser Glu Ser Leu Pro Val
 50                  55                  60

Gln Cys Thr Asp Gly Ser Val Pro Glu Ala Gln Ser Ala Leu Asp Ser
 65                  70                  75                  80

Thr Ser Ser Met Gln Pro Ser Pro Val Ser Asn Gln Ser Leu Leu
                 85                  90                  95

Ser Glu Ser Val Ala Ser Ser Gln Leu Asp Ser Thr Ser Val Asp Lys
            100                 105                 110

Ala Val Pro Glu Thr Glu Asp Val Gln Ala Ser Val Ser Asp Thr Ala
            115                 120                 125

Gln Gln Pro Ser Glu Glu Gln Ser Lys Ser Leu Glu Lys Pro Lys Gln
130                 135                 140

Lys Lys Asn Arg Cys Phe Met Cys Arg Lys Val Gly Leu Thr Gly
145                 150                 155                 160

Phe Glu Cys Arg Cys Gly Asn Val Tyr Cys Gly Val His Arg Tyr Ser
                165                 170                 175

Asp Val His Asn Cys Ser Tyr Asn Tyr Lys Ala Asp Ala Ala Glu Lys
                180                 185                 190

Ile Arg Lys Glu Asn Pro Val Val Val Gly Glu Lys Ile Gln Lys Ile
            195                 200                 205
```

(2) INFORMATION FOR SEQ ID NO:4:

(i) SEQUENCE CHARACTERISTICS:
        (A) LENGTH: 1197 base pairs
        (B) TYPE: nucleic acid
        (C) STRANDEDNESS: single
        (D) TOPOLOGY: linear (vii) IMMEDIATE SOURCE:
        (A) LIBRARY: BRAINOT09
        (B) CLONE: 2151473

(xi) SEQUENCE DESCRIPTION: SEQ ID NO:4:

```
TCGGCGGCAT TACCTGTACC CATTCACCGG CGGCTACCGG CGGCGGCGCG CAGTGTTCAG    60

GCGGAGAGAC CCGCCGCCAG GAATTGAATC TGAAGTCTGC TGCAGTAAAA CACAGAAGGC   120

TTTAAAATGT TTTCTTGCAT AAAATTCAAA ACTTTTAAGT AGCTGCTTAT GAGAATAGGG   180

AAGGCAGAAA GCTAATGTCT GTCTCAAGAT ACAGGACAGC TGTTTGCTCA TCAACCTCAA   240

CTGTGTGTGC AACTGAGGAA CATGGCTCAA GAAACTAATC ACAGCCAAGT GCCTATGCTT   300

TGTTCCACTG GCTGTGGATT TTATGGAAAC CCTCGTACAA ATGGCATGTG TTCAGTATGC   360

TATAAAGAAC ATCTTCAAAG ACAGAATAGT AGTAATGGTA GAATAAGCCC ACCTGCAACC   420

TCTGTCAGTA GTCTGTCTGA ATCTTTACCA GTTCAATGCA CAGATGGCAG TGTGCCAGAA   480

GCCCAGTCAG CATTAGACTC TACATCTTCA TCTATGCAGC CCAGCCCTGT ATCAAATCAG   540

TCACTTTTAT CAGAATCTGT AGCATCTTCT CAATTGGACA GTACATCTGT GGACAAAGCA   600

GTACCTGAAA CAGAAGATGT GCAGGCTTCA GTATCAGACA CAGCACAGCA GCCATCTGAA   660

GAGCAAAGCA AGTCTCTTGA AAAACCGAAA CAAAAAAAGA ATCGCTGTTT CATGTGCAGG   720

AAGAAAGTGG GACTTACTGG GTTTGAATGC CGGTGTGGAA ATGTTTACTG TGGTGTACAC   780
```

```
CGTTACTCAG ATGTACACAA TTGCTCTTAC AATTACAAAG CCGATGCTGC TGAGAAAATC       840

AGAAAAGAAA ATCCAGTAGT TGTTGGTGAA AAGATCCAAA AGATTTGAAC TCCTGCTGGA       900

ATACAAAATT CTTGAGCATC TGCAAACTAA AAATTGACTT GAGGTTTTTT TTTTCCTAGT       960

CATTGGGAAT GTAGAGCAGT GTATCTTGCA TGTCATCGGA AGAATAGATT TTTGTTTTGG      1020

TTTTGTTTTG AAAATGACTC TGAACATTTA TTTCCATTGC AATTTCTGTG GCTGAGGAGA      1080

CTTAAACTTT ACAAGTATTA TCCTTTTAAG ATCATTTTAA TTTTAGTTGA GTGCAGAGGG      1140

CTTTTATAAC AAACCGTGCA GAAATTTTGG AGGGCTGTGA TTTTTCCAGT ATTAAAC        1197
```

(2) INFORMATION FOR SEQ ID NO:5:

(i) SEQUENCE CHARACTERISTICS:
        (A) LENGTH: 250 amino acids
        (B) TYPE: amino acid
        (C) STRANDEDNESS: single
        (D) TOPOLOGY: linear (vii) IMMEDIATE SOURCE:
        (A) LIBRARY: 397581
        (B) CLONE: GenBank (xi) SEQUENCE DESCRIPTION: SEQ ID NO:5:

```
Met Ala Thr Lys Gln Ala His Lys Arg Leu Thr Lys Glu Tyr Lys Leu
 1               5                  10                  15

Met Val Glu Asn Pro Pro Tyr Ile Leu Ala Arg Pro Asn Glu Asp
                20                  25                  30

Asn Ile Leu Glu Trp His Tyr Ile Ile Thr Gly Pro Ala Asp Thr Pro
                35                  40                  45

Tyr Lys Gly Gly Gln Tyr His Gly Thr Leu Thr Phe Pro Ser Asp Tyr
 50                  55                  60

Pro Tyr Lys Pro Pro Ala Ile Arg Met Ile Thr Pro Asn Gly Arg Phe
 65                  70                  75                  80

Lys Pro Asn Thr Arg Leu Cys Leu Ser Met Ser Asp Tyr His Pro Asp
                85                  90                  95

Thr Trp Asn Pro Gly Trp Ser Val Ser Thr Ile Leu Asn Gly Leu Leu
                100                 105                 110

Ser Phe Met Thr Ser Asp Glu Ala Thr Thr Gly Ser Ile Thr Thr Ser
                115                 120                 125

Asp His Gln Lys Lys Thr Leu Ala Arg Asn Ser Ile Ser Tyr Asn Thr
 130                 135                 140

Phe Gln Asn Val Arg Phe Lys Leu Ile Phe Pro Glu Val Val Gln Glu
145                 150                 155                 160

Asn Val Glu Thr Leu Glu Lys Arg Lys Leu Asp Glu Gly Asp Ala Ala
                165                 170                 175

Asn Thr Gly Asp Glu Thr Glu Asp Pro Phe Thr Lys Ala Ala Lys Glu
                180                 185                 190

Lys Val Ile Ser Leu Glu Glu Ile Leu Asp Pro Glu Asp Arg Ile Arg
                195                 200                 205

Ala Glu Gln Ala Leu Arg Gln Ser Glu Asn Asn Ser Lys Lys Asp Gly
 210                 215                 220

Lys Glu Pro Asn Asp Ser Ser Ser Met Val Tyr Ile Gly Ile Ala Ile
225                 230                 235                 240

Phe Leu Phe Leu Val Gly Leu Phe Met Lys
                245                 250
```

(2) INFORMATION FOR SEQ ID NO:6:

(i) SEQUENCE CHARACTERISTICS:
    (A) LENGTH: 221 amino acids
    (B) TYPE: amino acid
    (C) STRANDEDNESS: single
    (D) TOPOLOGY: linear (vii) IMMEDIATE SOURCE:
    (A) LIBRARY: GenBank
    (B) CLONE: 1749704

(xi) SEQUENCE DESCRIPTION: SEQ ID NO:6:

Tyr Lys Arg Leu Met Lys Glu Tyr Leu Ala Leu Gln Lys Asn Pro Phe
1               5                   10                  15

Glu Leu Val Asp Ala Lys Pro Ala Thr Glu Asn Ile Leu Glu Trp His
            20                  25                  30

Tyr Ile Ile Thr Gly Pro Pro Asp Thr Pro Tyr Glu Gly Gly Gln Tyr
            35                  40                  45

His Gly Thr Leu Ile Phe Pro Pro Asp Tyr Pro Phe Lys Pro Pro Ala
    50                  55                  60

Ile Arg Met Ile Thr Pro Ser Gly Arg Phe Gln Thr Asn Thr Arg Leu
65                  70                  75                  80

Cys Leu Ser Phe Ser Asp Phe His Pro Lys Ser Trp Asn Pro Ser Trp
                85                  90                  95

Met Val Ser Thr Ile Leu Val Gly Leu Val Ser Phe Met Thr Ser Asp
            100                 105                 110

Glu Ile Thr Thr Gly Gly Ile Val Thr Ser Glu Ser Thr Arg Arg Thr
        115                 120                 125

Tyr Ala Lys Asp Thr Lys Arg Phe Asn Ile Met Asp Asn Pro Lys Phe
    130                 135                 140

Leu Ile Met Phe Pro Glu Leu Ile Asp Lys Asn Arg Glu Asp Ile Ala
145                 150                 155                 160

Lys Ala Ala Ala Glu Ala Ala Leu Ile Glu Pro Gln Gln Ile His Ser
                165                 170                 175

Thr Pro Val Ser Ser Asn Glu Cys Lys Lys Asn Glu Pro Phe Asn Ser
            180                 185                 190

Lys Gln Ser Trp Val Lys Ser Arg Trp Ser Ile Ala Val Leu Val Phe
        195                 200                 205

Phe Ala Leu Ala Leu Ala Arg Phe Phe Gly Ala Asp Ser
    210                 215                 220

(2) INFORMATION FOR SEQ ID NO:7:

(i) SEQUENCE CHARACTERISTICS:
        (A) LENGTH: 189 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1279278

(xi) SEQUENCE DESCRIPTION: SEQ ID NO:7:

Met Glu Asn Glu Gln Gln Gln Ala Gln Thr Ala Pro Ser Cys Arg Ala
1               5                   10                  15

Gly Cys Gly Phe Phe Gly Ala Ser Ala Thr Glu Gly Tyr Cys Ser Gln
            20                  25                  30

Cys Phe Lys Asn Thr Leu Lys Arg Gln Gln Asp Thr Val Arg Leu Thr
        35                  40                  45

Ser Pro Val Val Ser Pro Ser Ser Met Ala Ala Thr Ser Ser Ala Leu

```
        50                  55                  60
Lys Ser Glu Pro Ser Ser Val Asp Met Cys Met Lys Ala Ala Val Ser
65                  70                  75                  80

Val Ser Asp Glu Thr Ala Lys Met Asp Cys Glu Asp Ile Ile Asn Val
                85                  90                  95

Cys Asp Gln Ile Asn Asp Asp Ser Val Thr Val Ala Glu Ser Thr Ala
                100                 105                 110

Pro Thr Thr Ile Thr Val Asp Val Pro Val Pro Val Lys Lys Ala Asn
                115                 120                 125

Arg Cys His Met Cys Lys Lys Arg Val Gly Leu Thr Gly Phe Ser Cys
                130                 135                 140

Arg Cys Gly Gly Leu Tyr Cys Gly Asp His Arg Tyr Asp Gln Ala His
145                 150                 155                 160

Asn Cys Gln Phe Asp Tyr Lys Thr Met Glu Arg Glu Thr Ile Arg Lys
                165                 170                 175

Asn Asn Pro Val Val Ser Asp Lys Val Gln Arg Ile
                180                 185

(2) INFORMATION FOR SEQ ID NO:8:

(i) SEQUENCE CHARACTERISTICS:
        (A) LENGTH: 46 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 998680

(xi) SEQUENCE DESCRIPTION: SEQ ID NO:8:

Cys Arg Cys Gly Asn Leu Phe Cys Gly Leu His Arg Tyr Ser Asp Lys
1               5                   10                  15

His Asn Cys Pro Tyr Asp Tyr Lys Ala Glu Ala Ala Lys Ile Arg
                20                  25                  30

Lys Glu Asn Pro Val Val Val Ala Glu Lys Ile Gln Arg Ile
                35                  40                  45
```

UBIQUITIN CONJUGATION PROTEINS

This application is a divisional application of U.S. application Ser. No. 08/861,269, filed May 21, 1997 now U.S. Pat. No. 5,817,494.

FIELD OF THE INVENTION

This invention relates to nucleic acid and amino acid sequences of two new ubiquitin conjugation system proteins and to the use of these sequences in the diagnosis, prevention, and treatment of cancer, immune disorders, smooth muscle disorders, and viral infections.

BACKGROUND OF THE INVENTION

The ubiquitin conjugation system (UCS) is a major pathway for the degradation of cellular proteins in eukaroytic cells and in some bacteria. The UCS mediates the elimination of abnormal proteins and regulates the half-lives of important regulatory proteins that control cellular processes such as gene transcription and cell cycle progression. The UCS is implicated in the degradation of mitotic cyclic kinases, oncoproteins, tumor suppressor genes such as p53, viral proteins, cell surface receptors associated with signal transduction, transcriptional regulators, and mutated or damaged proteins (Ciechanover, A. (1994) Cell 79:13–21).

The process of ubiquitin conjugation and protein degradation occurs in four principal steps (Jentsch, S. (1992) Annu. Rev. Genet. 26:179–207). First ubiquitin (Ub), a small, heat stable protein (76 amino acids) is activated by a ubiquitin-activating enzyme (E1) in an ATP dependent reaction which binds the C-terminus of Ub to the thiol group of an internal cysteine residue in E1. Second, activated Ub is transferred to one of several Ub-conjugating enzymes (E2). Different ubiquitin-dependent proteolytic pathways employ structurally similar, but distinct ubiquitin-conjugating enzymes that are associated with recognition subunits which direct them to proteins carrying a particular degradation signal. E2 then links the Ub molecule through its C-terminal glycine to an internal lysine (acceptor lysine) of a target protein. Additional Ub molecules may be added forming a multi-Ub chain structure. The ubiquinated protein is then recognized and degraded by proteasome, a large, multisubunit proteolytic enzyme complex, and Ub is released for reutilization.

Prior to activation, Ub is usually expressed as a fusion protein composed of an N-terminal ubiquitin and a C-terminal extension protein (CEP), or as a polyubiquitin protein with Ub monomers attached head to tail. CEPs bear similarities to a variety of nucleic acid binding regulatory proteins. Most are highly basic with up to 30% lysine and arginine residues, and many have nucleic acid-binding, zinc-finger domains (Monia, B. P. et al. (1989) J. Biol. Chem. 264:4093–4103). These Ub-CEP fusion proteins are rapidly processed by C-terminal hydrolases which cleave Ub from the C-terminal side releasing free Ub for the UCS. The fusion of Ub with CEPs may allow co-regulation of the UCS with the translational activity of the cell. Processing of the CEPs may also be required to localize CEPs or Ub to specific cellular sites where they carry out their function (Monia et al., supra).

The E2 (Ub-conjugating) enzymes are important for substrate specificity in different UCS pathways. All E2s have a conserved domain of approximately 16 kDa called the UBC domain that is at least 35% identical in all E2s and contains a centrally located cysteine residue required for ubiquitin-enzyme thiolester formation (Jentsch, supra). A highly conserved proline-rich element is located N-terminal to the active cysteine residue. Structural variations beyond this conserved domain are used to classify the E2 enzymes. Class I E2s consist almost exclusively of the conserved UBC domain. Class II E2s have various unrelated C-terminal extensions that contribute to substrate specificity and cellular localization. Yeast class II enzymes UBC2 and UBC3 have highly acidic C-terminal extensions that promote interactions with basic substrates such as histones. Yeast UBC6 has a hydrophobic signal-anchor sequence that localizes the protein to the endoplasmic reticulum.

The discovery of new ubiquitin conjugation system proteins and the polynucleotides encoding them satisfies a need in the art by providing new diagnostic or therapeutic compositions useful in the treatment or prevention of cancer, immune disorders, smooth muscle disorders, and viral infections.

SUMMARY OF THE INVENTION

The present invention features two new human ubiquitin-conjugation system proteins hereinafter designated as UCSP-1 and UCSP-2, and collectively as UCSP, and characterized as having similarity to other ubiquitin-conjugation system proteins.

Accordingly, the invention features a substantially purified UCSP-1 and UCSP-2 having the amino acid sequences shown in SEQ ID NO:1 and SEQ ID NO:3, respectively.

One aspect of the invention features isolated and substantially purified polynucleotides that encode UCSP-1 and UCSP-2. In a particular aspect, the polynucleotides are the nucleotide sequences of SEQ ID NO:2 and SEQ ID NO:4, respectively.

The invention also relates to polynucleotide sequences comprising the complement of SEQ ID NO:2 or SEQ ID NO:4 or variants thereof. In addition, the invention features polynucleotide sequences which hybridize under stringent conditions to SEQ ID NO:2 or SEQ ID NO:4.

The invention additionally features fragments of the polynucleotides encoding UCSP, expression vectors and host cells comprising polynucleotides that encode UCSP and a method for producing UCSP using the vectors and host cells. The present invention also features antibodies which bind specifically to UCSP, and pharmaceutical compositions comprising substantially purified UCSP. The invention also features agonists and antagonists of UCSP. The invention also provides methods for treating disorders associated with expression of UCSP by administration of UCSP and methods for detection of polynucleotides encoding ubiquitin-conjugation proteins in a biological sample using the complement of the polynucleotide encoding UCSP.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of UCSP-1. The alignment was produced using MACDNASIS PRO™ software (Hitachi Software Engineering Co., Ltd., San Bruno, Calif.).

FIGS. 2A, 2B, 2C, and 2D show the amino acid sequence (SEQ ID NO:3) and nucleic acid sequence (SEQ ID NO:4) of UCSP-2. The alignment was produced using MACDNASIS PRO™ software.

FIGS. 3A and 3B show the amino acid sequence alignments among UCSP-1 (SEQ ID NO: 1), and the ubiquitin-conjugating enzyme, UBC6, from *Saccharomyces cerevisae* (GI 397581; SEQ ID NO:5) and *Shizosaccharomyces pombe*

(GI 1749704; SEQ ID NO:6). The alignment was produced using the multisequence alignment program of DNAS-TAR™ software (DNASTAR Inc, Madison Wis.).

FIG. 4 shows the amino acid sequence alignments among UCSP-2 (SEQ ID NO:3), a ubiquitin-like CEP protein from *Caenorhabditis elegans* (GI 1279278; SEQ ID NO:7), and cow (GI 998680; SEQ ID NO:8). The alignment was produced using the multisequence alignment program of DNASTAR™ software.

Figure 5A:
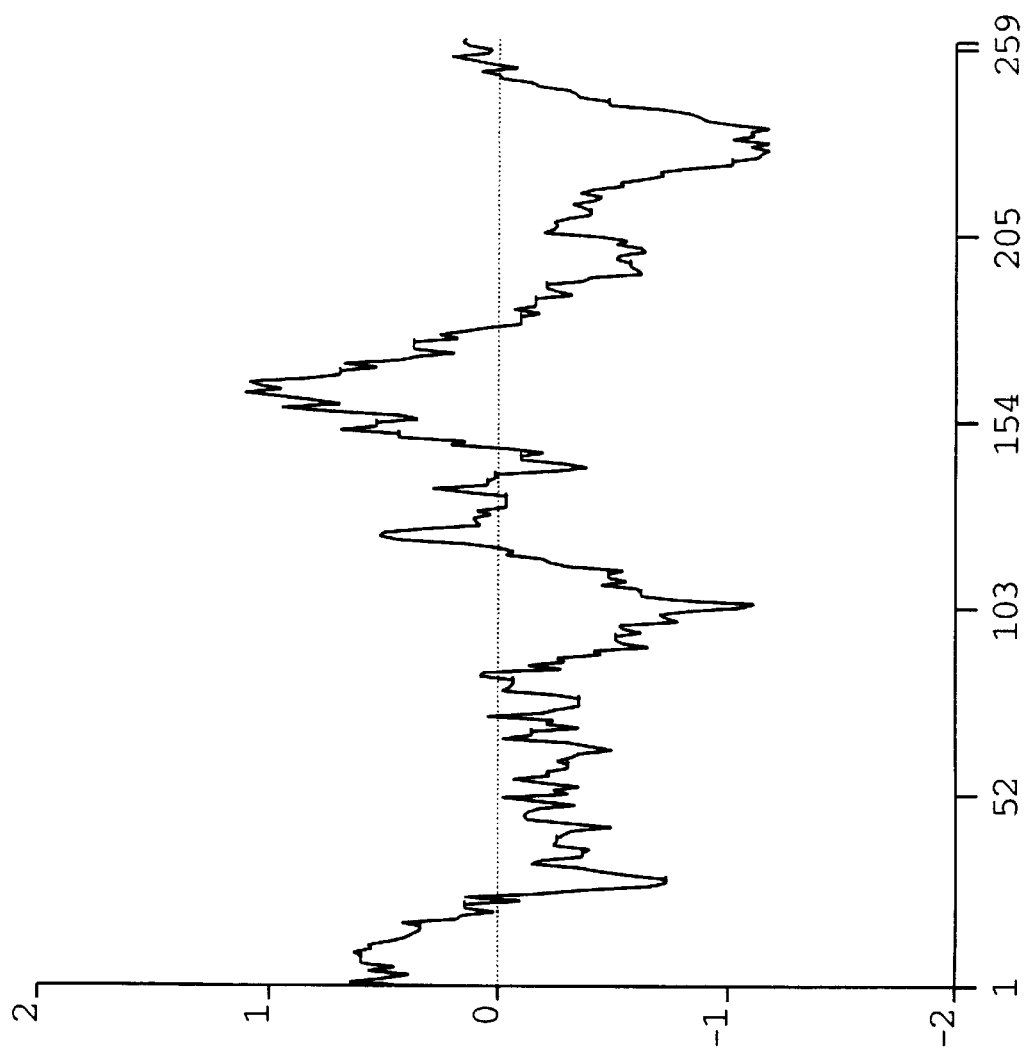
Figure 5B:
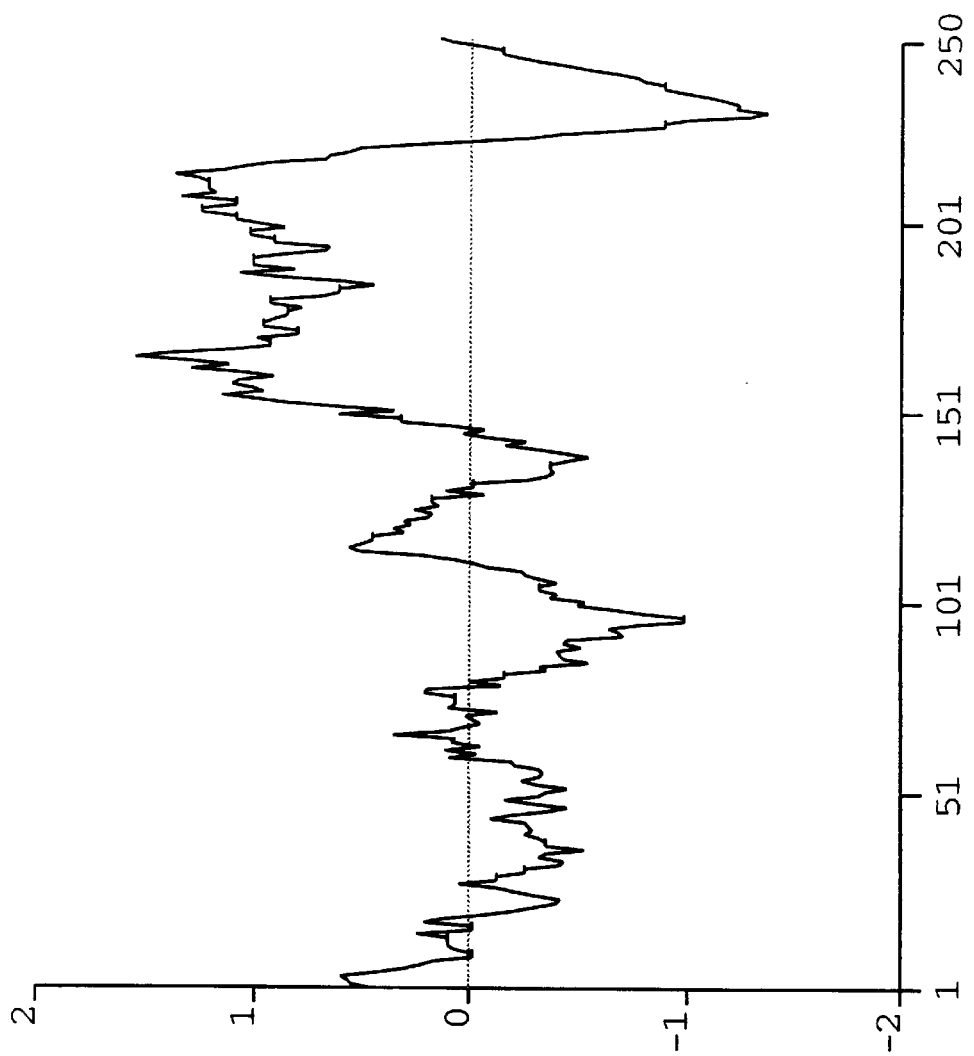
Figure 5C:
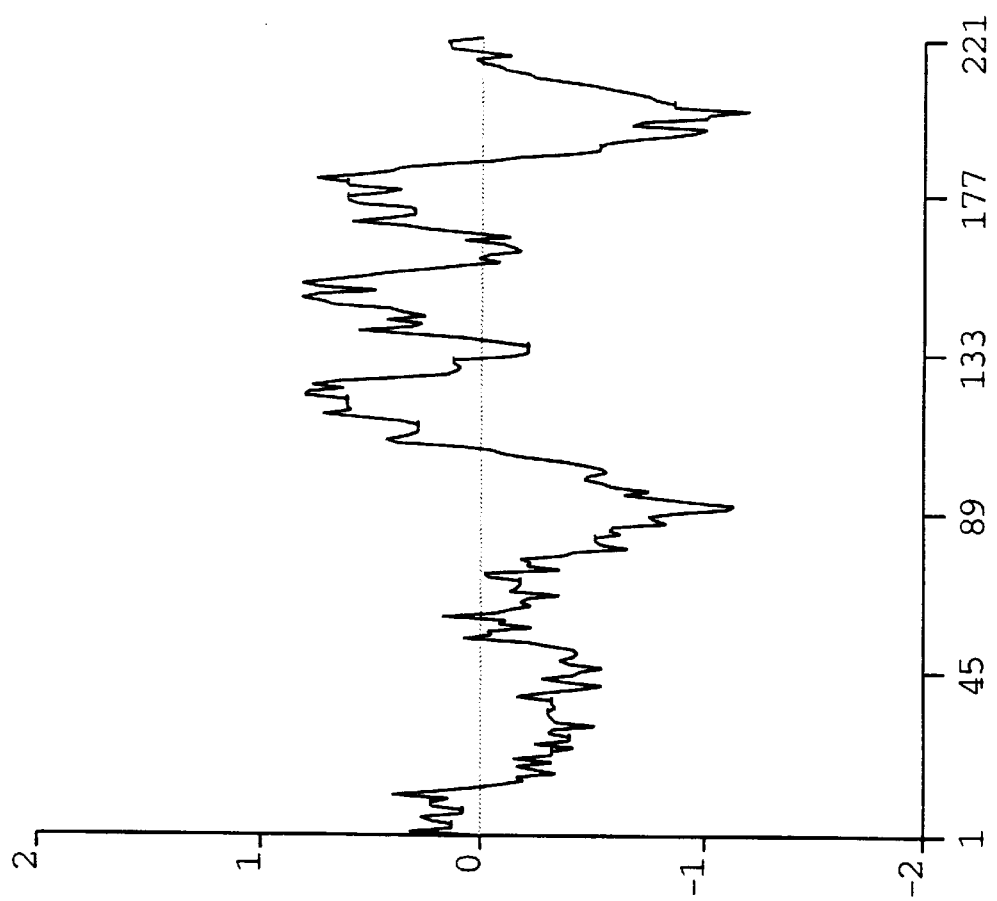

FIGS. 5A, 5B, and 5C show the hydrophobicity plots (MACDNASIS PRO™) for UCSP-1, SEQ ID NO:1; and UBC6 from *S. cerevisae,* SEQ ID NO:5, and *S. pombe,* SEQ ID NO:6. The positive X axis reflects amino acid position, and the negative Y axis, hydrophobicity.

Figure 6A:
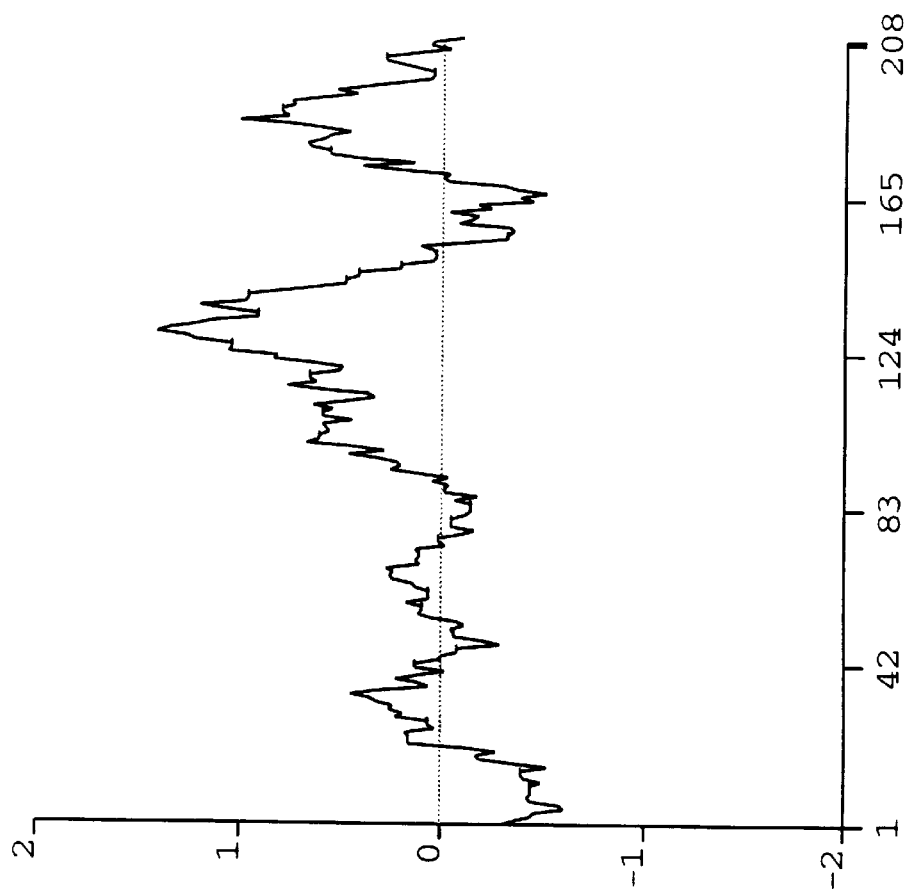
Figure 6B:
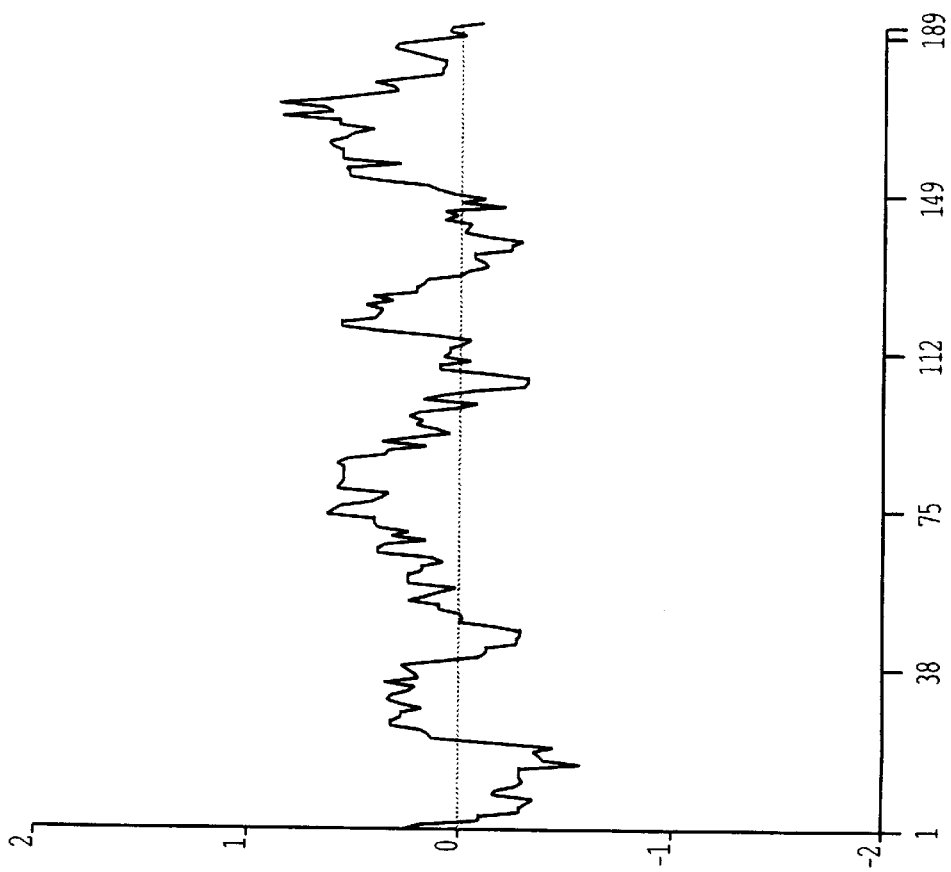

FIGS. 6A and 6B show the hydrophobicity plots (MACDNASIS PRO™) for UCSP-2, SEQ ID NO:3; and the ubiquitin-like CEP protein from *C. elegans,* SEQ ID NO:7). The positive X axis reflects amino acid position, and the negative Y axis, hydrophobicity.

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

UCSP, as used herein, refers to the amino acid sequences of substantially purified UCSP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer. Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of UCSP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic UCSP, or any oligopeptide thereof, to induce a specific immune response in appropriate animals or cells and to bind with specific antibodies.

The term "agonist", as used herein, refers to a molecule which, when bound to UCSP, causes a change in UCSP which modulates the activity of UCSP. Agonists may include proteins, nucleic acids, carbohydrates, or any other molecules which bind to UCSP.

The terms "antagonist" or "inhibitor", as used herein, refer to a molecule which, when bound to UCSP, blocks or modulates the biological or immunological activity of UCSP. Antagonists and inhibitors may include proteins, nucleic acids, carbohydrates, or any other molecules which bind to UCSP.

The term "modulate", as used herein, refers to a change or an alteration in the biological activity of UCSP. Modulation may be an increase or a decrease in protein activity, a change in binding characteristics, or any other change in the biological, functional or immunological properties of UCSP.

The term "mimetic", as used herein, refers to a molecule, the structure of which is developed from knowledge of the structure of UCSP or portions thereof and, as such, is able to effect some or all of the actions of ubiquitin conjugation system protein-like molecules.

The term "derivative", as used herein, refers to the chemical modification of a nucleic acid encoding UCSP or the encoded UCSP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1 or SEQ ID NO:3" encompasses the full-length human UCSP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding UCSP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding UCSP in a sample and thereby correlates with expression of the transcript from the polynucleotide encoding the protein.

"Alterations" in the polynucleotide of SEQ ID NO: 2 or SEQ ID NO:4, as used herein, comprise any alteration in the sequence of polynucleotides encoding UCSP including deletions, insertions, and point mutations that may be detected using hybridization assays. Included within this definition is the detection of alterations to the genomic DNA sequence which encodes UCSP (e.g., by alterations in the pattern of restriction fragment length polymorphisms capable of hybridizing to SEQ ID NO:2 or SEQ ID NO:4), the inability of a selected fragment of SEQ ID NO: 2 or SEQ ID NO:4 to hybridize to a sample of genomic DNA (e.g., using allele-specific oligonucleotide probes), and improper or unexpected hybridization, such as hybridization to a locus other than the normal chromosomal locus for the polynucleotide sequence encoding UCSP (e.g., using fluorescent in situ hybridization [FISH] to metaphase chromosome spreads).

As used herein, the term "antibody" refers to intact molecules as well as fragments thereof, such as Fa, $F(ab')_2$, and Fv, which are capable of binding the epitopic determinant. Antibodies that bind UCSP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of new human ubiquitin conjugation system proteins (UCSP), the polynucleotides encoding UCSP, and the use of these compositions for the diagnosis, prevention, or treatment of cancer, immune disorders, smooth muscle disorders, and viral infections.

Nucleic acids encoding the human UCSP-1 of the present invention were first identified in Incyte Clone 2029018 from the epidermal breast keratinocyte cDNA library (KERANOT02) through a computer search for amino acid sequence alignments. A consensus sequence, SEQ ID NO:2, was derived from the following overlapping and/or extended nucleic acid sequences: Incyte Clones 429101/BLADNOT01, 1684744/PROSNOT15, 1426101/BEPINON01, 2029018/KERANOT02, and 2047078/THP1T7T01.

In one embodiment, the invention encompasses a polypeptide comprising the amino acid sequence of SEQ ID NO:1 as shown in FIGS. 1A, 1B, 1C, and 1D. UCSP-1 is 259 amino acids in length and has several potential protein kinase phosphorylation sites. Potential casein kinase II phosphorylation sites are located at T54 and S96 of UCSP-1. Potential protein kinase C phosphorylation sites are located at S5, S6, T14, T138, S178, and T248. Potential tyrosine kinase phosphorylation sites are located at Y21 and Y56. Cysteine residues located at C33, C89, C94, and C157 represent potential disulfide bridging sites. As shown in FIGS. 3A and 3B, UCSP has chemical and structural homology with UBC6 from S. cerevisiae (GI 395781; SEQ ID NO:5) and S. pombe (GI 971980; SEQ ID NO:6). In particular, UCSP-1 shares 43% and 40% identity with UBC6 from S. cerevisiae and S. pombe, respectively. UCSP-1 shares several features common to UBC enzymes. C94 in UBSP-1 is the active cysteine residue centrally located in the UBC domain of all UBC enzymes that is necessary for thiolester formation with Ub. It is conserved in both the S. cerevisiae and S. pombe UBC6. The region surrounding this active center is also highly conserved in the three proteins. The proline-rich element N-terminal to the active cysteine residue is seen in UCSP—between approximately residues P66 and P83. The potential casein kinase II phosphorylation sites in UCSP-1 are shared by the S. pombe UBC6, as is the potential protein kinase C phosphorylation site at T138. As illustrated by FIGS. 5A, 5B, and 5C, UCSP and the S. cerevisiae and S. pombe UBC6 proteins have rather similar hydrophobicity plots. In particular, a prominent peak of hydrophobicity is evident at the N-terminal end of all three proteins that corresponds to the signal-anchor sequence of UBC6. Northern analysis shows the expression of UCSP-1 in various libraries, 50% of which are associated with cancer and immortalized cell lines and 33% of which are associated with smooth muscle and the sympathetic nervous system.

Nucleic acids encoding the human UCSP-2 of the present invention were first identified in Incyte Clone 2151473 from the fetal brain cDNA library (BRAINOT09) through a computer search for amino acid sequence alignments. A consensus sequence, SEQ ID NO:2, was derived from the following overlapping and/or extended nucleic acid sequences: Incyte Clones 2606447/LUNGTUT07, 375303/LUNGNOT02, and 2151473/BRAINOT09.

In another embodiment, the invention encompasses a polypeptide comprising the amino acid sequence of SEQ ID NO:3 as shown in FIGS. 2A, 2B, 2C, and 2D. UCSP-2 is 208 amino acids in length and has potential N-linked glycosylation sites at N6, N42, N92, and N180. Cysteine residues located at C14, C18, C30, C37, C149, C152, C163, C165, C170, and C181 represent potential disulfide bridging sites. Several potential casein kinase II phosphorylation sites are located at S57, S70, S76, S103, T108, S123, and T159. As shown in FIG. 4, UCSP-2 shares chemical and structural homology with ubiquitin-like CEPs from C. elegans (GI 1279278; SEQ ID NO:7), and cow (GI 998680; SEQ ID NO:8). In particular, UCSP-2 shares 40% and 80% identity with the C. elegans and cow CEPs. UCSP-2 and the two CEPs are highly basic in their C-terminal regions where they share the highest degree of homology. The isoelectric point (pI) for UCSP-2 beginning at approximately residue 121 and extending to the C-terminus is 9.22. The corresponding values for the C. elegans and cow CEPs are 9.05 and 9.13, respectively. All of the cysteine residues in UCSP-2 with the exception of C66 are shared by the C. elegans CEP. In particular, the conservation and spacing of cysteine and histidine residues in the C-terminal region between C163 and C181 suggests a potential zinc finger, nucleic acid-binding domain. As shown in FIGS. 6A and 6B, UCSP-2 and C. elegans CEP have rather similar hydrophobicity plots. Northern analysis shows the expression of UCSP-2 in various libraries 46% of which are associated with cancer and immortalized cell lines and 13% of which are associated with inflammation and the immune response.

The invention also encompasses UCSP variants. A preferred UCSP variant is one having at least 80%, and more preferably 90%, amino acid sequence identity to the UCSP amino acid sequence (SEQ ID NO:1 or SEQ IS NO:3). A most preferred UCSP variant is one having at least 95% amino acid sequence identity to SEQ ID NO:1 or SEQ ID NO:3.

The invention also encompasses polynucleotide which encode UCSP. Accordingly, any nucleic acid sequence which encodes the amino acid sequence of UCSP can be used to generate recombinant molecules which express UCSP. In a particular embodiment, the invention encompasses the polynucleotide comprising the nucleic acid sequence of SEQ ID NO:2 or SEQ ID NO:4 as shown in FIGS. 1A, 1B, 1C, and 1D or FIGS. 3A and 3B, respectively.

It will be appreciated by those skilled in the art that as a result of the degeneracy of the genetic code, a multitude of nucleotide sequences encoding UCSP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring UCSP, and all such variations are to be considered as being specifically disclosed.

Although nucleotide sequences which encode UCSP and its variants are preferably capable of hybridizing to the nucleotide sequence of the naturally occurring UCSP under appropriately selected conditions of stringency, it may be advantageous to produce nucleotide sequences encoding UCSP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding UCSP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode UCSP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding UCSP or any portion thereof.

Also encompassed by the invention are polynucleotide sequences that are capable of hybridizing to the claimed nucleotide sequences, and in particular, those shown in SEQ ID NO:2 od SEQ ID NO:4, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding UCSP which are encompassed by the invention include deletions, insertions, or substitutions of different nucleotides resulting in a polynucleotide that encodes the same or a functionally equivalent UCSP. The encoded protein may also contain deletions, insertions, or substitutions of amino acid residues which produce a silent change and result in a functionally equivalent UCSP. Deliberate amino acid substitutions may be made on the basis of similarity in polarity, charge, solubility, hydrophobicity, hydrophilicity, and/or the amphipathic nature of the residues as long as the biological activity of UCSP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding UCSP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase 1, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.).

Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding UCSP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, to J. D. et al. (1991; Nucleic Acids Res. 19:3055–3060). Additionally, one may use PCR, nested primers, and PROMOTERFINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode UCSP, or fusion proteins or functional equivalents thereof, may be used in recombinant DNA molecules to direct expression of UCSP in appropriate host cells. Due to the inherent degeneracy of the genetic code, other DNA sequences which encode substantially the same or a functionally equivalent amino acid sequence may be produced and these sequences may be used to clone and express UCSP.

As will be understood by those of skill in the art, it may be advantageous to produce UCSP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter UCSP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding UCSP may be ligated to a heterologous sequence to encode a fusion protein. For example, to screen peptide libraries for inhibitors of UCSP activity, it may be useful to encode a chimeric UCSP protein that can be recognized by a commercially available antibody. A fusion protein may also be engineered to contain a cleavage site located between the UCSP encoding sequence and the heterologous protein sequence, so that UCSP may be cleaved and purified away from the heterologous moiety.

In another embodiment, sequences encoding UCSP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of UCSP, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of UCSP, or any part thereof, may be altered during direct synthesis and/or combined using chemical methods with sequences from other proteins, or any part thereof, to produce a variant polypeptide.

In order to express a biologically active UCSP, the nucleotide sequences encoding UCSP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding UCSP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding UCSP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding UCSP, vectors based on SV40 or EBV may be used with an appropriate selectable marker.

In bacterial systems, a number of expression vectors may be selected depending upon the use intended for UCSP. For example, when large quantities of UCSP are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding UCSP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding UCSP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express UCSP. For example, in one such system, *Autographa californica* nuclear polyhedrosis virus (AcNPV) is used as a vector to express foreign genes in *Spodoptera frugiperda* cells or in Trichoplusia larvae. The sequences encoding UCSP may be cloned into a non-essential region of the virus, such as the polyhedrin gene, and placed under control of the polyhedrin promoter. Successful insertion of UCSP will render the polyhedrin gene inactive and produce recombinant virus lacking coat protein. The recombinant viruses may then be used to infect, for example, *S. frugiperda* cells or Trichoplusia larvae in which UCSP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding UCSP may be ligated into an adenovirus transcription/translation complex consisting of the late promoter and tripartite leader sequence. Insertion in a non-essential E1 or E3 region of the viral genome may be used to obtain a viable virus which is capable of expressing UCSP in infected host cells (Logan. J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding UCSP. Such signals include the ATG initiation codon and adjacent sequences. In cases where sequences encoding UCSP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express UCSP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$or aprt$^-$cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding UCSP is inserted within a marker gene sequence, recombinant cells containing sequences encoding UCSP can be identified by the absence of marker gene function. Alternatively, a marker gene can be placed in tandem with a sequence encoding UCSP under the control of a single promoter. Expression of the marker gene in response to induction or selection usually indicates expression of the tandem gene as well.

Alternatively, host cells which contain the nucleic acid sequence encoding UCSP and express UCSP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding UCSP can be detected by DNA—DNA or DNA-RNA hybridization or amplification using probes or portions or fragments of polynucleotides encoding UCSP. Nucleic acid amplification based assays involve the use of oligonucleotides or oligomers based on the sequences encoding UCSP to detect transformants containing DNA or RNA encoding UCSP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of UCSP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on UCSP is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding UCSP include oligolabeling, nick translation, end-labeling or PCR amplification using a labeled nucleotide. Alternatively, the sequences encoding UCSP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding UCSP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode UCSP may be designed to contain signal sequences which direct secretion of UCSP through a prokaryotic or eukaryotic cell membrane. Other recombinant constructions may be used to join sequences encoding UCSP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and UCSP may be used to facilitate purification. One such expression vector provides for expression of a fusion protein containing UCSP and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying UCSP from the fusion protein. A discussion of vectors which contain fusion proteins is provided in Kroll. D. J. et al. (1993; DNA Cell Biol. 12:441–453).

In addition to recombinant production, fragments of UCSP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of UCSP may be chemically synthesized separately and combined using chemical methods to produce the full length molecule.

THERAPEUTICS

Chemical and structural homology exists among UCSP-1 and UBC6 from *S. cerevisiae* and *S.pombe.* In addition, northern analysis shows the expression of UCSP-1 in tissues associated with cancer and smooth muscle. UCSP therefore appears to be associated with the development of cancer and smooth muscle disorders. In addition, the known function of the UCS in processing viral proteins implicates UCSP-1 in the development of viral diseases.

The UCS is involved in the degradation of certain oncogenic proteins. Therefore a decrease in the level or activity of UCSP-1 appears to be associated with the development of cancer. Therefore in one embodiment, UCSP-1 or a fragment or derivative thereof, may be administered to a subject to treat or prevent cancer, including astrocytoma, glioma, ganglioneuroma, neurocytoma, neuroblastoma, adenocarcinoma, sarcoma, melanoma, lymphoma, leukemia, and myeloma. In particular, types of cancer may include, but are not limited to, cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing UCSP-1, or a fragment or a derivative thereof, may also be administered to a subject to treat or prevent any of the types of cancer listed above.

A decrease in the level or activity of UCSP-1 also appears to be associated with the development of smooth muscle disorders. Therefore in another embodiment, UCSP-1 or a fragment or derivative thereof, may be administered to a subject to treat or prevent a smooth muscle disorder. A smooth muscle disorder is defined as any impairment or alteration in the normal action of smooth muscle and may include, but is not limited to, angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia. Smooth muscle is a component of the blood vessels, gastrointestinal tract, heart, and uterus.

In another embodiment, a vector capable of expressing UCSP-1, or a fragment or a derivative thereof, may also be administered to a subject to treat or prevent any of the smooth muscle disorders listed above.

An increase in the level or activity of UCSP-1 appears to be associated with the development of viral diseases. Therefore in another embodiment, an antagonist or inhibitor of UCSP-1 may be administered to a subject to treat or prevent viral diseases. Viral diseases may include, but are not limited to, adenoviruses (ARD, pneumonia), arenaviruses (lymphocytic choriomeningitis), bunyaviruses (Hantavirus), coronaviruses (pneumonia, chronic bronchitis), hepadnaviruses (hepatitis), herpesviruses (HSV, VZV, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (HIV, HTLV), rhabdoviruses (rabies), rotaviruses (gastroenteritis), and togaviruses (encephalitis, rubella,). In one aspect of this embodiment, antibodies which are specific for UCSP-1 may be used directly as an antagonist, or indirectly as a targeting or delivery mechanism for bringing a pharmaceutical agent to cells or tissues which express UCSP-1.

In another embodiment, the complement of the polynucleotide encoding UCSP-1 or an antisense molecule may be administered to a subject to treat or prevent any of the viral diseases listed above.

Chemical and structural homology exists among UCSP-2 and ubiquitin-like CEP proteins from *Caenorhabditis elegans* and cow. In addition, northern analysis shows the expression of UCSP-2 in tissues associated with cancer and the immune system. UCSP-2 therefore appears to be associated with the development of cancer and immune disorders.

A decrease in the level or activity of UCSP-2 appears to be associated with the development of cancer. Therefore in another embodiment, UCSP-2, or a fragment or derivative thereof, may be administered to a subject to treat or prevent cancer, including astrocytoma, glioma, ganglioneuroma, neurocytoma, neuroblastoma, adenocarcinoma, sarcoma, melanoma, lymphoma, leukemia, and myeloma. In particular, types of cancer may include, but are not limited to, cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing UCSP-2, or a fragment or a derivative thereof, may also be administered to a subject to treat or prevent any of the types of cancer listed above.

An increase in the level or activity of UCSP-2 appears to be associated with the development of immune disorders. Therefore in another embodiment, an antagonist or inhibitor of UCSP-2 may be administered to a subject to treat or prevent an immune disorder. Such disorders may include, but are not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect of this embodiment, antibodies which are specific for UCSP-2 may be used directly as an antagonist, or indirectly as a targeting or delivery mechanism for bringing a pharmaceutical agent to cells or tissues which express UCSP-2.

In another embodiment, the complement of the polynucleotide encoding UCSP-2 or an antisense molecule may be administered to a subject to treat or prevent any of the immune disorders listed above.

In other embodiments, any of the therapeutic proteins, antagonists, antibodies, agonists, antisense sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of UCSP may be produced using methods which are generally known in the art. In particular, purified UCSP may be used to produce antibodies or to screen libraries of pharmaceutical agents to identify those which specifically bind UCSP.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with UCSP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to UCSP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of UCSP amino acids may be fused with those of another protein such as keyhole limpet hemocyanin and antibody produced against the chimeric molecule.

Monoclonal antibodies to UCSP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce UCSP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter. G. et al. (1991) Nature 349:293–299).

Antibody fragments which contain specific binding sites for UCSP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between UCSP and its specific antibody. A two-site, monoclonal-based immunoassay utilizing monoclonal antibodies reactive to two non-interfering UCSP epitopes is preferred, but a competitive binding assay may also be employed (Maddox, supra).

In another embodiment of the invention, the polynucleotides encoding UCSP, or any fragment thereof, or antisense molecules, may be used for therapeutic purposes. In one aspect, antisense to the polynucleotide encoding UCSP may be used in situations in which it would be desirable to block the transcription of the mRNA. In particular, cells may be transformed with sequences complementary to polynucleotides encoding UCSP. Thus, antisense molecules may be used to modulate UCSP activity, or to achieve regulation of gene function. Such technology is now well known in the art, and sense or antisense oligomers or larger fragments, can be designed from various locations along the coding or control regions of sequences encoding UCSP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding UCSP. These techniques are described both in Sambrook et al. (supra) and in Ausubel et al. (supra).

Genes encoding UCSP can be turned off by transforming a cell or tissue with expression vectors which express high levels of a polynucleotide or fragment thereof which encodes UCSP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding UCSP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding UCSP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding UCSP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of UCSP, antibodies to UCSP, mimetics, agonists, antagonists, or inhibitors of UCSP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose. and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of UCSP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example UCSP or fragments thereof, antibodies of UCSP, agonists, antagonists or inhibitors of UCSP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages, and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind UCSP may be used for the diagnosis of conditions or diseases characterized by expression of UCSP, or in assays to monitor patients being treated with UCSP, agonists, antagonists or inhibitors. The antibodies useful for diagnostic purposes may be prepared in the same manner as those described above for therapeutics. Diagnostic assays for UCSP include methods which utilize the antibody and a label to detect UCSP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring UCSP are known in the art and provide a basis for diagnosing altered or abnormal levels of UCSP expression. Normal or standard values for UCSP expression are established by combining body fluids or cell extracts taken from normal mammalian subjects, preferably human, with antibody to UCSP under conditions suitable for complex formation. The amount of standard complex formation may be quantified by various methods, but preferably by photometric means. Quantities of UCSP expressed in subject samples, control and disease, from biopsied tissues are compared with the standard values. Deviation between standard and subject values establishes the parameters for diagnosing disease.

In another embodiment of the invention, the polynucleotides encoding UCSP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of UCSP may be correlated with disease. The diagnostic assay may be used to distinguish between absence, presence, and excess expression of UCSP, and to monitor regulation of UCSP levels during therapeutic intervention.

In one aspect, hybridization with PCR probes which are capable of detecting polynucleotide sequences, including genomic sequences, encoding UCSP or closely related molecules, may be used to identify nucleic acid sequences which encode UCSP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding UCSP, alleles, or related sequences.

Probes may also be used for the detection of related sequences, and should preferably contain at least 50% of the nucleotides from any of the UCSP encoding sequences. The hybridization probes of the subject invention may be DNA or RNA and derived from the nucleotide sequence of SEQ ID NO:2 or from genomic sequence including promoter, enhancer elements, and introns of the naturally occurring UCSP.

Means for producing specific hybridization probes for DNAs encoding UCSP include the cloning of nucleic acid sequences encoding UCSP or UCSP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding UCSP may be used for the diagnosis of conditions or diseases which are associated with expression of UCSP. Examples of such conditions or diseases include cancer such as cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; smooth muscle disorders such as angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia; viral diseases such as adenoviruses (ARD, pneumonia), arenaviruses (lymphocytic choriomeningitis), bunyaviruses (Hantavirus), coronaviruses (pneumonia, chronic bronchitis), hepadnaviruses (hepatitis), herpesviruses (HSV, VZV, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (HIV, HTLV), rhabdoviruses (rabies), rotaviruses (gastroenteritis), and togaviruses (encephalitis, rubella,); and immune disorders such as AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. The polynucleotide sequences encoding UCSP may be used in Southern or northern analysis, dot blot, or other membrane-based technologies; in PCR technologies; or in dip stick, pin, ELISA or chip assays utilizing fluids or tissues from patient biopsies to detect altered UCSP expression. Such qualitative or quantitative methods are well known in the art.

In a particular aspect, the nucleotide sequences encoding UCSP may be useful in assays that detect activation or induction of various cancers, particularly those mentioned above. The nucleotide sequences encoding UCSP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding UCSP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of UCSP, a normal or standard profile for expression is established. This may be accomplished by combining body fluids or cell extracts taken from normal subjects, either animal or human, with a sequence, or a fragment thereof, which encodes UCSP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding UCSP may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of UCSP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode UCSP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding UCSP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, UCSP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between UCSP and the agent being tested, may be measured.

Another technique for drug screening which may be used provides for high throughput screening of compounds having suitable binding affinity to the protein of interest as described in published PCT application WO84/03564. In this method, as applied to UCSP large numbers of different small test compounds are synthesized on a solid substrate, such as plastic pins or some other surface. The test compounds are reacted with UCSP, or fragments thereof, and washed. Bound UCSP is then detected by methods well known in the art. Purified UCSP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding UCSP specifically compete with a test compound for binding UCSP. In this manner, the antibodies can be used to detect the presence of any peptide which shares one or more antigenic determinants with UCSP.

In additional embodiments, the nucleotide sequences which encode UCSP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I KERANOT02 cDNA Library Construction

The KERANOT02 cDNA library was constructed from cryopreserved normal epidermal keratinocytes purchased from Clonetics (San Diego, Calif.). The tissue donor was a 30 year old Afro-American female whose skin was resected during elective breast reduction surgery. At the time of surgery, the donor was taking ferrous sulfate in preparation for the surgery, and a routine blood test was unremarkable except for a slight elevation of serum alanine transferase.

One ampule of $7.6 \times 10^5$ cells was cultured and expanded in media and supplements provided by Clonetics, following the recommended protocol, except that use of bovine pituitary extract was omitted. After a single passage, $3 \times 10^7$ cells were harvested and lysed using a Brinkmann Homogenizer Polytron PT-3000 (Brinkmann Instruments, Westbury N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with phenol chloroform pH 8.0, precipitated using 0.3 M sodium acetate and 2.5 volumes of ethanol, resuspended in RNAse-free water and DNase treated at 37° C. RNA extraction and precipitation was repeated as before. The mRNA was then isolated using the Qiagen Oligotex kit (QIAGEN Inc; Chatsworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL, Gaithersburg, Md.). cDNAs were fractionated on a Sepharose CL4B column (Cat. #275105-01; Pharmacia), and those cDNAs exceeding 400 bp were ligated into PSPORTI plasmid. The plasmid PSPORTI was subsequently transformed into DH5a™ competent cells (Cat. #18258-012; Gibco/BRL).

II BRAINOT09 cDNA Library Construction

The BRAINOT09 cDNA library was constructed from fetal brain tissue obtained from a 25-week-old Caucasian male (International Institute of Advanced Medicine, Exton, Pa.) who was delivered after 25 week gestation and died soon thereafter. Family history included diabetes in the mother.

The frozen tissue was homogenized and lysed using a Brinkmann Homogenizer Polytron-PT 3000 (Brinkmann Instruments, Inc., Westbury, N.Y.) in guanidinium isothiocyanate solution. The lysates were extracted once with acid phenol at pH 4.7 per Stratagene's RNA isolation protocol (Stratagene, Inc.). The RNA was extracted once with an equal volume of acid phenol, reprecipitated using 0.3 M sodium acetate and 2.5 volumes of ethanol, resuspended in DEPC-treated water and DNase treated for 25 min at 37° C. mRNAs were isolated using the Qiagen Oligotex kit (QIAGEN, Inc.; Chatworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105-01; Pharmacia), and those cDNAs exceeding 400 bp were ligated into PSPORTI plasmid. The plasmid PSPORTI was subsequently transformed into DH5a™ competent cells (Cat. #18258-012; Gibco/BRL).

III Isolation and Sequencing of cDNA Clones

Plasmid DNA was released from the cells and purified using the REAL Prep 96 Plasmid Kit (Catalog #26173; QIAGEN Inc). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) the cultures were incubated for 19 hours after the wells were inoculated and then lysed with 0.3 ml of lysis buffer; 3) following isopropanol precipitation, the plasmid DNA pellet was resuspended in 0.1 ml of distilled water. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with Peltier Thermal Cyclers (PTC200 from MJ Research, Watertown Mass.) and Applied Biosystems 377 or 373 DNA Sequencing Systems; and the reading frame was determined.

IV Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

V Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding UCSP occurs. Abundance and percent abundance are also reported. Abundance directly reflects the number of times a particular transcript is represented in a cDNA library, and percent abundance is abundance divided by the total number of sequences examined in the cDNA library.

VI Extension of UCSP-Encoding Polynucleotides

Nucleic acid sequence of Incyte Clone 2029018 or 2151473, or SEQ ID NO:2 or SEQ ID NO:4, respectively, is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |

-continued

| | |
|---|---|
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VII Labeling and Use of Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VIII Complementary Polynucleotide, Antisense Molecules

Polynucleotide complementary to the UCSP-encoding sequence, or any part thereof, or an antisense molecule is used to inhibit in vivo expression of naturally occurring UCSP. Although use of antisense oligonucleotides, comprising about 20 base-pairs, is specifically described, essentially the same procedure is used with larger cDNA fragments. An oligonucleotide based on the coding sequences of UCSP, as shown in FIGS. 1A, 1B, 1C and 1D or FIG. 2, is used to inhibit expression of naturally occurring UCSP. The complementary oligonucleotide is designed from the most unique 5' sequence as shown in FIGS. 1A, 1B, 1C and 1D or FIG. 2 and used either to inhibit transcription by preventing promoter binding to the upstream nontranslated sequence or translation of an UCSP-encoding transcript by preventing the ribosome from binding. Using an appropriate portion of the signal and 5' sequence of SEQ ID NO:2 or SEQ ID NO:4, an effective antisense oligonucleotide includes any 15–20 nucleotides spanning the region which translates into the signal or 5' coding sequence of the polypeptide as shown in FIGS. 1A, 1B, 1C and 1D or FIG. 2.

IX Expression of UCSP

Expression of UCSP is accomplished by subcloning the cDNAs into appropriate vectors and transforming the vectors into host cells. In this case, the cloning vector is used to express UCSP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of UCSP into the bacterial growth media which can be used directly in the following assay for activity.

IX Demonstration of UCSP Activity

UCSP-1

UCSP-1 activity may be measured by the ability of UBC6 enzymes to suppress translocation of proteins in yeast cells containing a defective sec61 gene (Jentsch, supra). SEC61 protein is involved in the translocation of certain other proteins (KAR2, CPY, and α-factor) across the endoplasmic reticulum in yeast cells. In mutant yeast cells containing a defective SEC61 protein subunit (sec61 mutants), the defective protein is degraded by a UBC6 dependent pathway. This degradation results in the accumulation of unprocessed precursors of KAR2, CPY, and α-factor. Double mutants defective in both UBC6 expression and normal SEC16 protein expression (sec16/ubc6) translocate proteins normally. UCSP-1 may therefore be measured by suppression of protein translocation in sec16/ubc6 cells transfected with the gene expressing UCSP-1. Accumulation of unprocessed precursors of KAR2, CPY, and α-factor are compared in the UCSP-1 transfected and untransfected sec16/ubc6 cells labeled with $^{35}$S-methionine. Proteins are immunoprecipitated with antibodies to KAR2, CPY, and α-factor and separated by immunoelectrophoresis. The accumulation of precursor proteins in UCSP-1 transfected cells is a measure of the UCSP-1 activity in these cells.

UCSP-2

UCSP-2 activity may be measured by degradation of a fusion protein containing ubiquitin conjugated through its C-terminal glycine to UCSP-2. UbCEP fusion proteins are rapidly degraded to free Ub and CEP in incubations containing cell-free rabbit reticulocyte extracts (Monia, et al., supra). This extract contains enzymes required for Ub processing and conjugation of Ub with target proteins. A suitable vector must first be constructed for expression of the Ub-UCSP-2 fusion protein in E. coli or S. cerevisiae. The purified Ub-UCSP-2 is then incubated in a reaction buffer (50 mM Tris-HCl, pH 7.5, 1 mM dithiothreitol) containing rabbit reticulocyte extract. Reactions are carried out at 37° C. for 20 to 40 minutes and are stopped by heating to 68° C. for 5 minutes in the presence of 0.1% SDS. Proteins are separated by polyacrylamide gel electrophoresis. The amount of free UCSP-2 recovered is proportional to the activity of UCSP-2 in the fusion protein.

X Production of UCSP Specific Antibodies

UCSP that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis. Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring UCSP Using Specific Antibodies

Naturally occurring or recombinant UCSP is substantially purified by immunoaffinity chromatography using antibodies specific for UCSP. An immunoaffinity column is constructed by covalently coupling UCSP antibody to an activated chromatographic resin, such as CnBr-activated Sepharose (Pharmacia & Upjohn). After the coupling, the resin is blocked and washed according to the manufacturer's instructions.

Media containing UCSP is passed over the immunoaffinity column, and the column is washed under conditions that allow the preferential absorbance of UCSP (e.g., high ionic strength buffers in the presence of detergent). The column is eluted under conditions that disrupt antibody/UCSP binding (eg, a buffer of pH 2–3 or a high concentration of a chaotrope, such as urea or thiocyanate ion), and UCSP is collected.

XII Identification of Molecules Which Interact with UCSP

UCSP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled UCSP, washed and any wells with labeled UCSP complex are assayed. Data obtained using different concentrations of UCSP are used to calculate values for the number, affinity, and association of UCSP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified ubiquitin conjugation system protein comprising the amino acid sequence of SEQ ID NO:1.

2. A pharmaceutical composition comprising an isolated and purified ubiquitin conjugation system protein of claim 1 in conjunction with a suitable pharmaceutical carrier.

* * * * *